US00PP29408P3

(12) United States Plant Patent
Stemkens

(10) Patent No.: US PP29,408 P3
(45) Date of Patent: Jun. 19, 2018

(54) ***ACHILLEA* PLANT NAMED 'ACBZ0004'**

(50) Latin Name: *Achillea millefolium*
Varietal Denomination: ACBZ0004

(71) Applicant: Henricus Godefridus Wilhelmus Stemkens, Enkhuizen (NL)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 15/330,861

(22) Filed: Nov. 8, 2016

(65) Prior Publication Data

US 2018/0132406 P1 May 10, 2018

(51) Int. Cl.
*A01H 5/02* (2018.01)

(52) U.S. Cl.
USPC ..... Plt./263.1

(58) Field of Classification Search
USPC ..... Plt./263.1
CPC ..... A01H 5/025; A01H 5/02; A01H 5/0205; A01H 5/00
See application file for complete search history.

(56) References Cited

PUBLICATIONS

Pluto Upov Plant Variety Database Oct. 24, 2017 for *Achillea* Acbz0004 retrieved on Oct. 26, 2017, retrieved from the Internet at http://www.upov.int/pluto/en/index.jsp, one page (Year: 2017).*

* cited by examiner

*Primary Examiner* — June Hwu
(74) *Attorney, Agent, or Firm* — C. A. Whealy

(57) ABSTRACT

A new and distinct cultivar of *Achillea* plant named 'ACBZ0004', characterized by its relatively compact, upright and uniform plant habit; moderately vigorous growth habit; freely basal branching habit; early and freely flowering habit with plants remaining in flower for a long period time; inflorescences with dark red purple-colored ray florets that resist "bleaching" with development; and good garden performance.

1 Drawing Sheet

Botanical designation: *Achillea millefolium.*
Cultivar denomination: 'ACBZ0004'.

CROSS-REFERENCED TO CLOSELY-RELATED APPLICATIONS

Title: *Achillea* Plant Named 'ACBZ0003'
Applicant: Henricus Godefridus Wilhelmus Stemkens
Filed: Nov. 8, 2016
Ser. No. 15/330,860

BACKGROUND OF THE INVENTION

The present invention relates to a new and distinct cultivar of *Achillea* plant, botanically known as *Achillea millefolium*, and hereinafter referred to by the name 'ACBZ0004'.

The new *Achillea* plant is a product of a planned breeding program conducted by the Inventor in Enkhuizen, The Netherlands. The objective of the breeding program is to create new compact and early-flowering *Achillea* plants with uniform plant habit and large inflorescences.

The new *Achillea* plant originated from an open-pollination in Enkhuizen, The Netherlands in August, 2009 of a proprietary selection of *Achillea millefolium* identified as code number L4332-1, not patented, as the female, or seed, parent with an unknown selection of *Achillea millefolium* as the male, or pollen, parent. The new *Achillea* plant was discovered and selected by the Inventor as a single flowering plant from within the progeny of the stated open-pollination in a controlled greenhouse environment in Enkhuizen, The Netherlands on Jul. 5, 2010.

Asexual reproduction of the new *Achillea* plant by vegetative tip cuttings in a controlled environment in Enkhuizen, The Netherlands since Jul. 6, 2010, has shown that the unique features of this new *Achillea* plant are stable and reproduced true to type in successive generations.

SUMMARY OF THE INVENTION

Plants of the new *Achillea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ACBZ0004'. These characteristics in combination distinguish 'ACBZ0004' as a new and distinct *Achillea* plant:

1. Relatively compact, upright and uniform plant habit.
2. Moderately vigorous growth habit.
3. Freely basal branching habit.
4. Early and freely flowering habit with plants remaining in flower for a long period time.
5. Inflorescences with dark red purple-colored ray florets that resist "bleaching" with development.
6. Good garden performance.

Plants of the new *Achillea* differ from plants of the female parent selection in the following characteristics:

1. Plants of the new *Achillea* are taller than plants of the female parent selection.
2. Plants of the new *Achillea* flower for a longer period of time than plants of the female parent selection.
3. Plants of the new *Achillea* and the female parent selection differ in ray floret color as plants of the female parent selection have lighter-colored ray florets.

Plants of the new *Achillea* can be compared to plants of *Achillea millefolium* 'ACBZ0003', disclosed in U.S. Plant patent application Ser. No. 15/330,860. In side-by-side comparisons, plants of the new *Achillea* differ from plants of 'ACBZ0003' in ray floret color as plants of 'ACBZ0003' have greyed purple-colored ray florets. In addition, plants of the new *Achillea* have smaller leaves with petioles than plants of 'ACBZ0003' which are sessile.

Plants of the new *Achillea* can also be compared to plants of *Achillea tomentosa*×*Achillea millefolium* 'Desred', disclosed in U.S. Plant Pat. No. 22,333. In side-by-side comparisons, plants of the new *Achillea* differ from plants of 'Desred' in the following characteristics:

1. Plants of the new *Achillea* are not as freely basal branching as plants of 'Desred'.
2. Plants of the new *Achillea* and 'Desred' differ in ray floret color as plants of 'Desred' have red-colored ray florets.
3. Ray florets of plants of the new *Achillea* resist "bleaching" whereas ray florets of plants of 'Desred' "bleach" in color to yellow.

BRIEF DESCRIPTION OF THE PHOTOGRAPHS

The accompanying photographs illustrate the overall appearance of the new *Achillea* plant showing the colors as true as it is reasonably possible to obtain in colored reproductions of this type. Colors in the photographs may differ slightly from the color values cited in the detailed botanical description which accurately describe the colors of the new *Achillea* plant.

The photograph at the bottom of the sheet is a side perspective view of a typical flowering plant of 'ACBZ0004' grown in a container.

The photograph at the top of the sheet is a close-up view of a typical flowering plant of 'ACBZ0004'.

DETAILED BOTANICAL DESCRIPTION

Plants used for the aforementioned photographs and following observations and measurements describe plants grown during the early summer in 20-cm containers in a polyethylene-covered greenhouse in Lancaster, Pa. and under cultural practices typical of commercial *Achillea* production. During the production of the plants, day temperatures averaged 23.8° C. and night temperatures averaged 18.3° C. Plants were 20 weeks old when the photographs and description were taken. In the following description, color references are made to The Royal Horticultural Society Colour Chart, 2007 Edition, except where general terms of ordinary dictionary significance are used.

Botanical classification: *Achillea millefolium* 'ACBZ0004'.

Parentage:

*Female, or seed, parent*.—Proprietary selection of *Achillea millefolium* identified as code number L4332-1, not patented.

*Male, or pollen, parent*.—Unknown selection of *Achillea millefolium*, not patented.

Propagation:

*Type*.—Terminal vegetative cuttings.

*Time to initiate roots, summer*.—About seven days at temperatures about 20° C.

*Time to initiate roots, winter*.—About nine days at temperatures about 20° C.

*Time to produce a rooted cutting, summer*.—About 18 days at temperatures about 20° C.

*Time to produce a rooted cutting, winter*.—About 21 days at temperatures about 20° C.

*Root description*.—Fine, fibrous; typically creamy white in color, actual color of the roots is dependent on substrate composition, water quality, fertilizer type and formulation, substrate temperature and physiological age of roots.

*Rooting habit*.—Freely branching habit; dense.

Plant description:

*Plant and growth habit*.—Compact, upright and uniform plant habit; moderately vigorous growth habit; freely basal branching habit with about 32 basal branches developing per plant.

*Plant height*.—About 24 cm.

*Plant diameter or spread*.—About 34 cm.

*Basal branches*.—Length: About 27 cm. Diameter: About 2.5 mm. Internode length: About 1 cm to 3.2 cm. Aspect: Mostly upright. Strength: Moderately strong. Texture: Lanulose; longitudinally ridged. Color: Close to 148B.

Leaf description:

*Arrangement*.—Alternate, simple.

*Length*.—About 6.4 cm.

*Width*.—About 2 cm.

*Shape*.—Overall, oblanceolate; feathery and fern-like.

*Apex*.—Acute, three-pointed.

*Base*.—Truncate.

*Margin*.—Deeply and finely dissected, pinnatisect.

*Texture, upper surface*.—Pubescent.

*Texture, lower surface*.—Lanulose.

*Venation pattern*.—Pinnate.

*Color*.—Developing leaves, upper surface: Close to N137A. Developing leaves, lower surface: Close to N137B. Fully expanded leaves, upper surface: Close to N137B; venation, close to 147C. Fully expanded leaves, lower surface: Close to 147B; venation, close to 147C.

*Petioles*.—Length: About 1.6 cm. Width: About 2 mm. Texture, upper and lower surfaces: Lanulose. Color, upper and lower surfaces: Close to 148B.

Inflorescence description:

*Arrangement and habit*.—Rotate composite inflorescence form; inflorescences arranged in terminal or axillary compound corymbs; corymbs are mostly flat-topped to slightly rounded; freely flowering habit with about 90 to 110 inflorescences per terminal corymb; corymbs positioned above the foliar plane and face mostly upright.

*Fragrance*.—Faint; spicy and sour.

*Time to flower*.—Plants begin flowering during the late spring and early summer in Pennsylvania and continue to flower throughout the summer.

*Inflorescence longevity*.—Inflorescences last about seven to ten days; inflorescences persistent; ray florets maintain color and resist "bleaching".

*Inflorescence buds*.—Height: About 5 mm. Diameter: About 3 mm. Shape: Ovoid. Color, when showing color: Close to 70B.

*Inflorescence diameter*.—About 1 cm.

*Disc diameter*.—About 3 mm.

*Receptacle diameter*.—About 3 mm.

*Receptacle height*.—About 4 mm.

*Receptacle shape*.—Rounded conical.

*Receptacle color*.—Close to 148B to 148C.

*Ray florets*.—Quantity and arrangement: About five in a single whorl. Length: About 4 mm. Width: About 3 mm. Shape: Roughly oval. Apex: Rounded to slightly emarginate. Base: Attenuate. Margin: Entire. Texture and luster, upper surface: Smooth, glabrous; velvety. Texture and luster, lower surface: Smooth, glabrous; matte. Aspect: Mostly horizontal. Color: When opening, upper surface: Close to 70B. When opening, lower surface: Close to 69C. Fully opened, upper surface: Close to 59A; with development, color becoming closer to N79B to N79C. Fully opened, lower surface: Close to 84B to 84C; with development, color becoming closer to 84D.

*Disc florets*.—Quantity and arrangement: About 20 massed at the center of the receptacle. Length: About 6 mm. Diameter: About 1.5 mm. Shape: Tubular; apex, five-pointed. Texture: Smooth, glabrous. Color, immature: Apex: Close to 161D. Mid-section: Close to 145B. Base: Close to 145D. Color, mature: Apex: Close to 84C. Mid-section: Close to 145B. Base: Close to 145D.

*Phyllaries*.—Quantity and arrangement: About 20 arrange in about two to three whorls; imbricate and tightly appressed to the ray florets. Length: About 4 mm. Width: About 1 mm. Shape: Lanceolate. Apex: Acute. Base: Truncate. Margin: Entire. Texture, upper surface: Smooth, glabrous. Texture, lower surface: Pubescent. Color, upper surface: Close to 146C. Color, lower surface: Close to 146A to 146B.

*Peduncles*.—Length: About 2.5 cm to 5 cm. Diameter: About 2 mm. Strength: Moderately strong. Aspect: Mostly upright. Texture: Lanulose. Color: Close to 147B.

*Reproductive organs*.—Androecium (present on disc florets only): Quantity: About five. Filament length: About 1 mm. Filament color: Close to 145D. Anther shape: Oblong. Anther length: About 1 mm. Anther color: Close to 17B. Pollen amount: Scarce. Pollen color: Close to 13A. Gynoecium (present on disc and ray florets): Quantity: One. Pistil length: About 4 mm. Stigma shape: Bi-parted. Stigma color: Close to 1.57D. Style length: About 2 mm. Style color: Close to 145D. Ovary color: Close to 145D.

*Seeds and fruits*.—Seed and fruit production has not been observed on plants of the new *Achillea* to date.

Pathogen & pest resistance: Plants of the new *Achillea* have not been shown to be resistant to pathogens and pests common to *Achillea* plants.

Garden performance: Plants of the new *Achillea* have been observed to have good garden performance and tolerate wind, rain and to tolerate temperatures ranging from about −15° C. to about 40° C.

It is claimed:

1. A new and distinct *Achillea* plant named 'ACBZ0004' as illustrated and described.

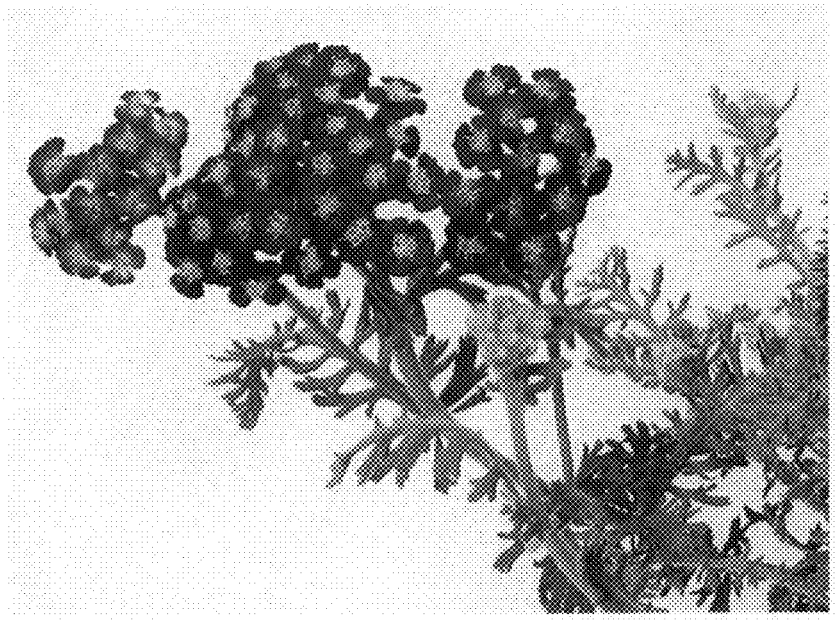
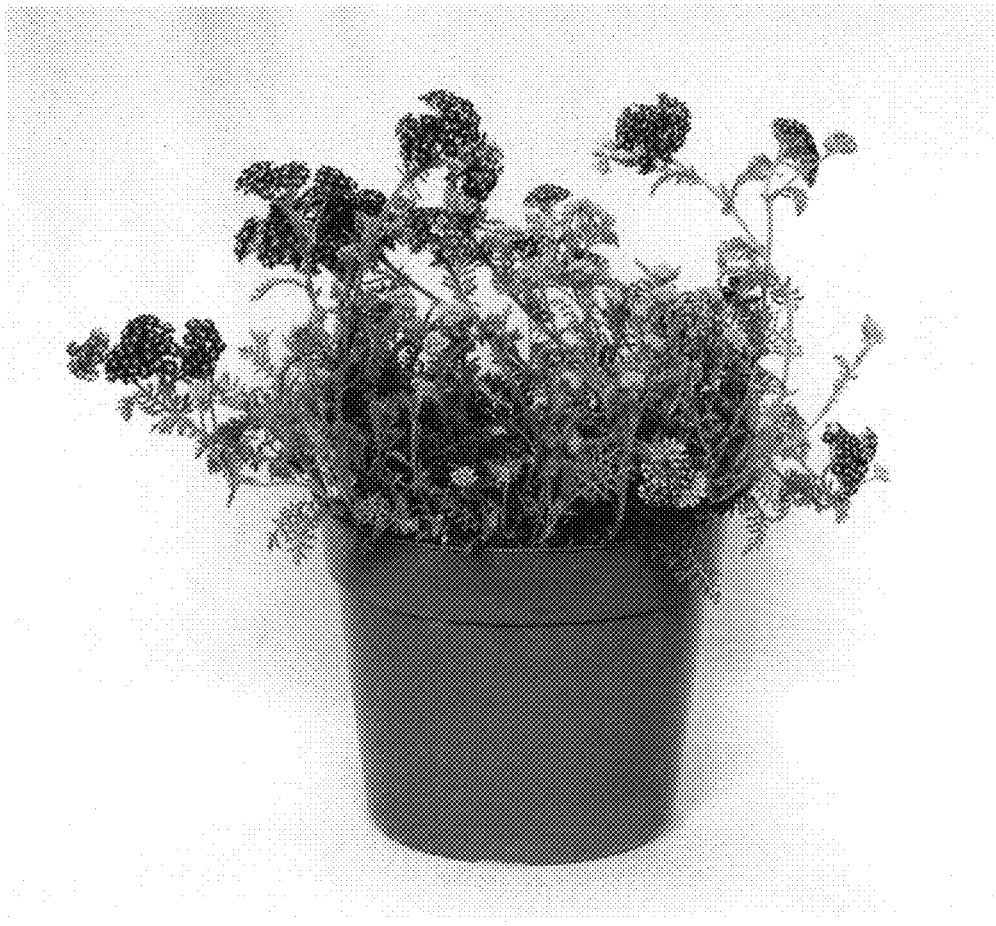

* * * * *